(12) United States Patent
Liu et al.

(10) Patent No.: US 12,402,907 B2
(45) Date of Patent: Sep. 2, 2025

(54) CUTTING BALLOON CATHETER WITH CONCEALED BLADES

(71) Applicant: BROSMED MEDICAL CO., LTD., Guangdong (CN)

(72) Inventors: Chaosheng Liu, Guangdong (CN); Zhijun Zhang, Guangdong (CN); Bin Li, Guangdong (CN)

(73) Assignee: BROSMED MEDICAL CO., LTD., Dongguan (CN)

( * ) Notice: Subject to any disclaimer, the term of this patent is extended or adjusted under 35 U.S.C. 154(b) by 221 days.

(21) Appl. No.: 18/359,583

(22) Filed: Jul. 26, 2023

(65) Prior Publication Data
US 2023/0363787 A1 Nov. 16, 2023

(30) Foreign Application Priority Data

Aug. 18, 2022 (CN) .......................... 202210996349.X

(51) Int. Cl.
*A61B 17/3207* (2006.01)
*A61B 17/00* (2006.01)
*A61M 25/10* (2013.01)

(52) U.S. Cl.
CPC .................. *A61B 17/32075* (2013.01); *A61B 2017/00287* (2013.01); *A61M 2025/1081* (2013.01); *A61M 2025/1086* (2013.01)

(58) Field of Classification Search
CPC ........ A61B 17/3207; A61B 17/320708; A61B 17/320725; A61B 17/32075; A61B 17/320783; A61B 2017/00287; A61B 2017/320716; A61B 2017/320733; A61B 2017/320741; A61B 2017/320755;
(Continued)

(56) References Cited

U.S. PATENT DOCUMENTS 5,324,261 A * 6/1994 Amundson ......... A61M 25/104
604/103.05
8,870,816 B2 * 10/2014 Chambers ........... A61M 25/104
604/103.05
(Continued)

FOREIGN PATENT DOCUMENTS

CN 108577937 A 9/2018
CN 112472228 A 3/2021
(Continued)

*Primary Examiner* — Elizabeth Houston
*Assistant Examiner* — Lindsey Bachman
(74) *Attorney, Agent, or Firm* — SHIMOKAJI IP

(57) ABSTRACT

A cutting balloon catheter with concealed blades is provided. A pressure channel communicated with the balloon is formed by a gap between the outer tube and the inner tube. The cutting assembly includes first support rings sleeved on the outer tube and a blade group, the first support rings are capable of generating radial elastic deformation and sliding freely. The push-pull tube is sleeved on the outer tube, and the protective bag is configured to encapsulate the balloon and the cutting assembly. When the cutting assembly is pushed to the balloon, after the balloon is expanded, the blade group cuts a section of the protective bag opposite to the balloon to expose the blade group. The catheter can pass through the complex and tortuous blood vessels to reach the lesion site, and realize effective cutting while reducing the damage to the blood vessels.

9 Claims, 8 Drawing Sheets

(58) Field of Classification Search
CPC .... A61B 2017/320766; A61M 25/104; A61M 2025/105; A61M 2025/1081
See application file for complete search history.

(56) References Cited

U.S. PATENT DOCUMENTS

| | | | |
|---|---|---|---|
| 10,561,438 B2* | 2/2020 | Boyle | A61M 25/104 |
| 2003/0093086 A1 | 5/2003 | Briggs et al. | |
| 2003/0144677 A1 | 7/2003 | Lary | |
| 2005/0137616 A1 | 6/2005 | Vigil | |
| 2007/0073329 A1* | 3/2007 | Hardert | A61M 25/104 |
| | | | 606/192 |
| 2007/0191811 A1* | 8/2007 | Berglund | A61M 25/104 |
| | | | 604/509 |
| 2008/0288041 A1 | 11/2008 | Holman et al. | |
| 2014/0088624 A1 | 3/2014 | Burton et al. | |
| 2014/0324079 A1* | 10/2014 | Silvestro | A61B 17/32075 |
| | | | 606/159 |
| 2017/0065796 A1* | 3/2017 | Fojtik | A61M 25/104 |
| 2019/0344054 A1 | 11/2019 | Slattery et al. | |
| 2024/0081856 A1* | 3/2024 | Casiraro | A61B 17/320725 |
| 2024/0374878 A1* | 11/2024 | Shekalim | A61B 17/221 |

FOREIGN PATENT DOCUMENTS

| | | |
|---|---|---|
| CN | 113877045 A | 1/2022 |
| JP | 2011098060 A | 5/2011 |
| JP | 2018027166 A | 2/2018 |
| JP | 2022048923 A | 3/2022 |

\* cited by examiner

CUTTING BALLOON CATHETER WITH CONCEALED BLADES

FIELD OF THE INVENTION

The present invention relates to the technical field of interventional treatment medical instruments, in particular to a cutting balloon catheter with concealed blades.

BACKGROUND OF THE INVENTION

Vascular interventional therapy is an important way of revascularization in the treatment of vascular stenosis. Balloon catheters are usually used as the main instrument for vascular interventional therapy. For some intravascular stenosis, such as calcification, plaque or fibrosis, conventional balloon catheters cannot effectively dilate the stenosis site. To solve this problem, balloon catheters with special functions such as cutting and scoring have been developed and used.

A cutting balloon catheter is provided with multiple blades arranged axially on the outer peripheral surface of the balloon, and the blades are configured to contact the lesion site when the balloon expands, thus cutting the lesion site and reducing the elastic retraction of the lesion site that is dilated.

Before the expansion of the balloon, the blades are located in the groove of the collapsed area of the balloon. When the balloon is expanded at the lesion location, the blades extend out of the balloon and performs regular cutting on the vascular lesion. In this way, irregular laceration on the blood vessel is small and the restenosis can be reduced. However, in the current cutting balloon catheter, due to the existence of blades and blade base, the diameter of the collapsed balloon is large, thus the passing ability of the catheter in the treatment of intravascular stenosis is poor, which requires other instruments to pretreat. In addition, the blades made of stainless steel are fixed on the balloon, thus have large hardness. In the prior art, a number of short blades are arranged at intervals and supported by a blade base that is bonded to the balloon by glue, thus the current cutting balloon catheter may only withstand a small bending. Therefore, based on the sharp and inflexible characteristics of the blades, it's not possible for the current cutting balloon catheter to pass through the tortuous blood vessel site during the pushing process, and there is a risk of damage to the normal blood vessel wall during the pushing. Especially in the expansion of the lesion site with a large angle, it's potential to cause vascular perforation and other adverse events. Therefore, the existing cutting balloon catheter is not suitable for treating with tortuous lesions and angulated lesions with an angle greater than 45 degrees.

In view of this, the technical problem to be solved by the invention is to provide an improved cutting balloon catheter, which has good processing ability of tortuous blood vessels, stenosis lesions and angulated lesions, and has safe cutting ability to reduce the risk of damage to normal blood vessels during surgery.

The invention provides a cutting balloon, which aims to improve the passing ability and safety of the cutting balloon, so as to pass through the complex and tortuous blood vessels to reach the lesion site to achieve effective cutting while reducing the damage to blood vessels.

SUMMARY OF THE INVENTION

An objective of the present invention is to provide a cutting balloon catheter with concealed blades, which can pass through the complex and tortuous blood vessels to reach the lesion site, and realize effective cutting while reducing the damage to the blood vessels.

To achieve the above objective, the present invention provides a cutting balloon catheter with concealed blades, including:

an inner tube and an outer tube sleeved on the inner tube, and the inner tube having a distal end penetrating out of the outer tube;

a collapsible balloon, having a proximal end connected with the distal end of the inner tube and a distal end connected with the inner tube, and a pressure channel communicated with the balloon being formed by a gap between the outer tube and the inner tube;

a cutting assembly, including a plurality of first support rings sleeved on the outer tube and a blade group arranged on each of the first support rings, wherein the plurality of the first support rings are arranged along an axial direction of the inner tube and capable of generating radial elastic deformation and sliding freely, and two adjacent blade groups are connected with one another through a first flexible member;

a push-pull tube, sleeved on the outer tube and having a distal end connecting with the blade group close to the push-pull tube through a second flexible member;

a tip, being a hollow structure and arranged on the distal end of the inner tube, wherein the tip has a taper structure and a proximal end provided with a stopper for preventing a forward movement of the cutting assembly; and a protective bag, having a distal end connected with the proximal end of the tip and a proximal end connected with the push-pull tube, and configured to encapsulate the balloon and the cutting assembly; wherein when the cutting assembly is pushed to the balloon by the push-pull tube, after the balloon is expanded, the blade group cuts a section of the protective bag opposite to the balloon so as to expose the blade group.

As a preferable embodiment, the blade group includes a plurality of blades arranged at intervals along an outer peripheral surface of each of first support rings.

As a preferable embodiment, each blade has a height of 0.5 mm to 5 mm and a length of 1 mm to 50 mm.

As a preferable embodiment, the cutting balloon catheter further includes an operating end arranged on the proximal ends of the inner tube, the outer tube and the push-pull tube, wherein the operating end is provided with a control structure connected with the push-pull tube, the control structure is configured to drive the push-pull tube to slide forward and backward along the outer tube, and the operating end is further provided with a Luer taper communicated with the pressure channel and a port communicated with a lumen of the inner tube.

As a preferable embodiment, the control structure includes a slot, an operating handle and a connecting member, the slot is arranged on an outer wall of the operating end and communicated with a cavity of the operating end, the operating handle is arranged in the slot and slidable along the slot, and the connecting member is respectively connected with the push-pull tube and the operating handle.

As a preferable embodiment, the cutting assembly further includes a second support ring located at the distal ends of all the first support rings and connected with the blade group through the first flexible member, the second support ring is rigid and capable of sliding freely, and an inner diameter of the second support ring is greater than an inner diameter of the proximal end of the tip and less than an outer diameter of the proximal end of the tip, so that a wall of the tip is served as the stopper.

As a preferable embodiment, the protective bag is provided with a first cutting line extended transversely and having a length equivalent to a length of the balloon.

As a preferable embodiment, the protective bag is further provided with a plurality of second cutting lines extended longitudinally and intersected with the first cutting line, each of the second cutting lines is opposite to one of the blade groups when the cutting assembly is pushed to the balloon.

As a preferable embodiment, the distal end of the push-pull tube and the inner tube of the balloon are respectively provided with a positioning member.

In comparison with the prior art, the cutting balloon catheter of the present invention has the following technical effects.

First, the cutting assembly is configured at the proximal end of the balloon and arranged separated from the balloon, and the balloon and the cutting assembly are packaged through the protective bag, therefore, the cutting assembly is concealed in the protective bag during the process of pushing the cutting assembly by the push-pull tube, which greatly reduces the risk of damage to normal blood vessels by the cutting assembly during the process of pushing.

Second, for the cutting assembly, multiple blade groups are connected together by flexible members and supported by a carrier that can generate radial elastic deformation, thus the cutting assembly has good overall bending performance, thereby improving the ability of cutting assembly to pass through tortuous blood vessels. In addition, for a lesion site that is curved, excessive cutting on the lesion site is effectively avoided, complications such as perforation and restenosis are avoided, and the cutting balloon catheter of the present invention is applicable to the lesion site in a wider angle.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

In order to describe the technical content, structural features, achieved objects and effects of the present invention in detail, the following detailed description is given in conjunction with the embodiments and the accompanying drawings.

It should be noted that the term "proximal end" herein generally refers to that end of the referred component close to the operator, and the term "distal end" refers to that end of the referred component away from the operator.

Figure 1:
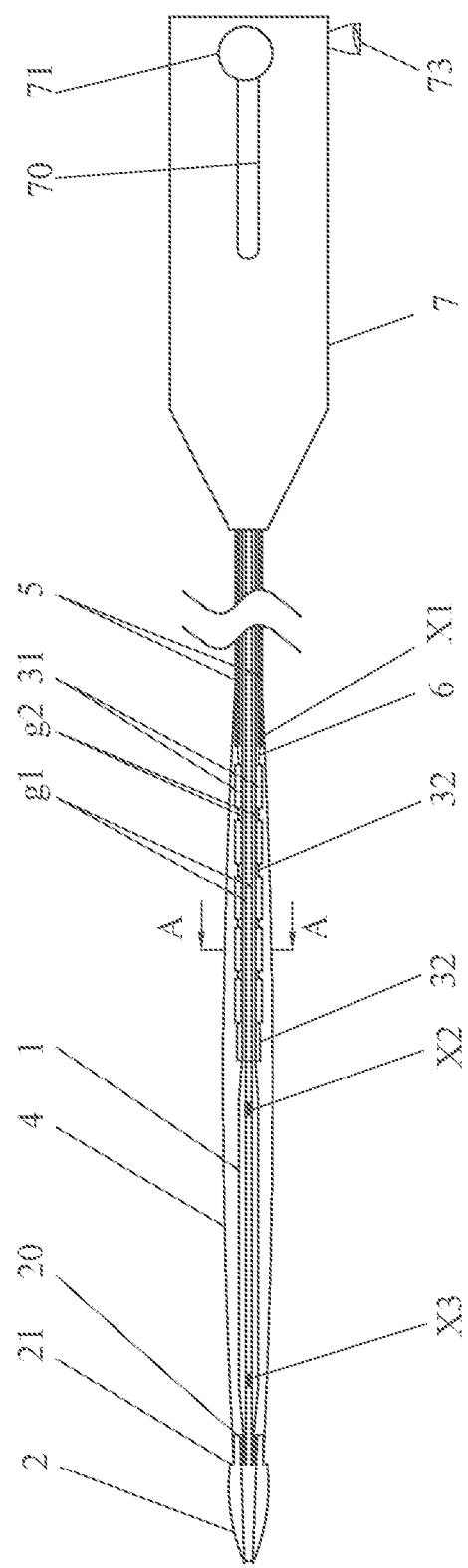
FIG. 1 is a plane view of a cutting balloon catheter according to an embodiment of the invention, wherein the cutting assembly is located behind the balloon.
Figure 2:
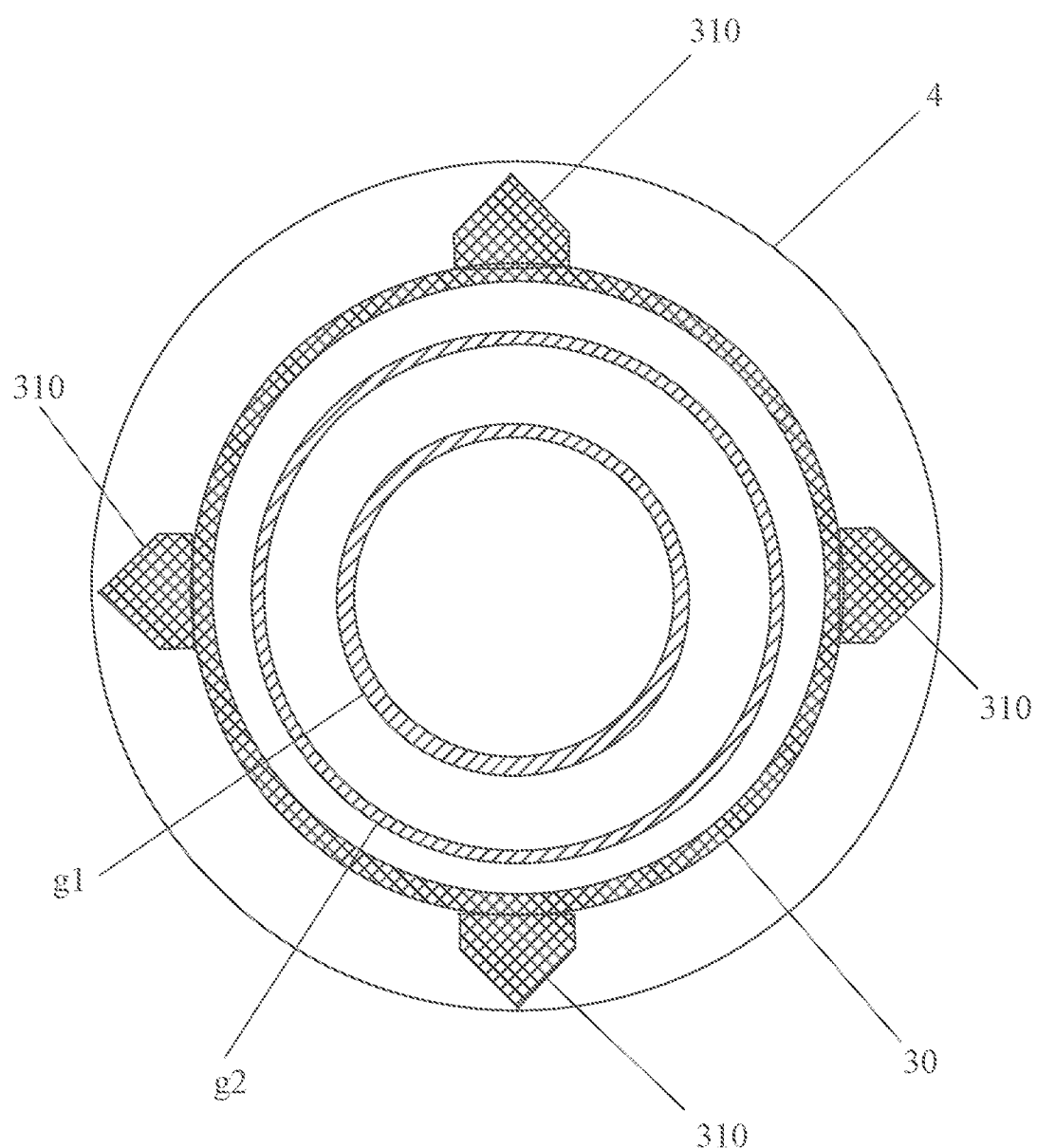
FIG. 2 is a longitudinal sectional view of portion A-A in FIG. 1.
Figure 3:
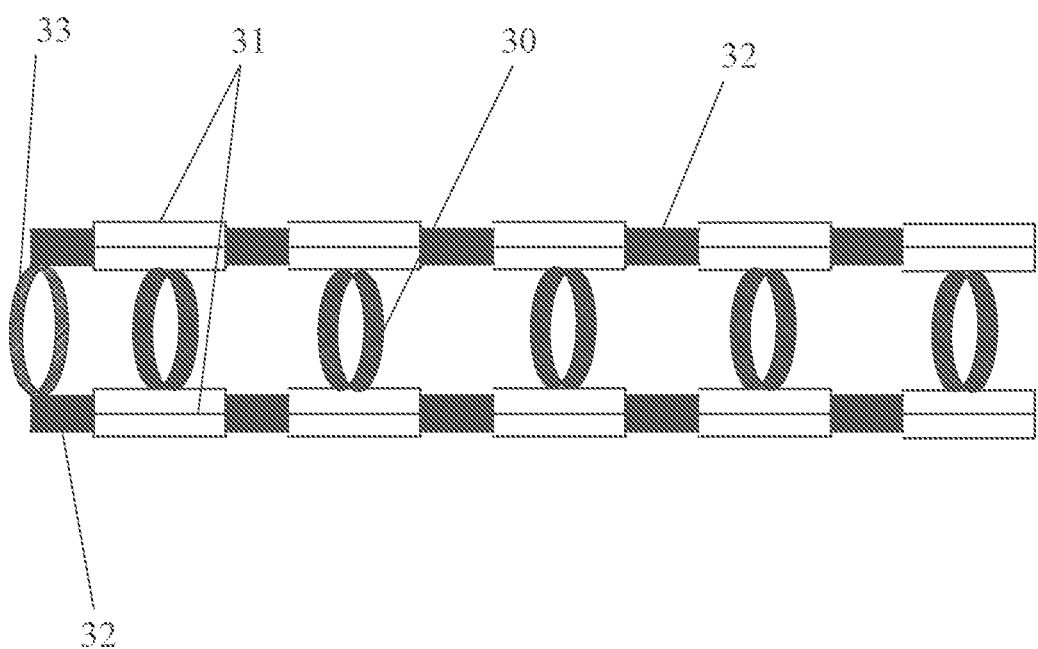
FIG. 3 is a plane view of a cutting assembly according to the embodiment of the invention.

The present embodiment discloses a cutting balloon catheter with concealed blades, which is used in vascular intervention to treat arteriovenous fistula stenosis, peripheral vascular stenosis, coronary artery stenosis, etc., to improve blood perfusion in patients. Specifically, as shown in FIG. 1 to FIG. 3, the cutting balloon catheter in the present embodiment includes an inner tube g1, an outer tube g2, a balloon 1, a cutting assembly (not labeled), a push-pull tube 5, a tip 2 and a protective bag 4.

The outer tube g2 is sleeved on the inner tube g1, and the distal end of the inner tube g1 is penetrated out of the outer tube g2. In this embodiment, a guide wire channel L1 (referring to FIG. 4) is formed in a lumen of the inner tube g1, that is, the inner tube g1 is suitable and configured for mounting a guide wire.

The balloon 1 is a collapsible balloon, that is, the balloon 1 may be expandable when filled with a medium so as to expand the blood vessels, and may be restored to a collapsed state when the medium is extracted. In this embodiment, the main body of balloon 1 is made of a semi-compliant or non-compliant material. The proximal end of balloon 1 is connected with the distal end of the outer tube g2, and the distal end of the balloon 1 is connected with the inner tube g1. The gap between the outer tube g2 and the inner tube g1 forms a pressure channel L2 (referring to FIG. 4) that is communicated with the balloon 1, by which the balloon 1 may be expanded or collapsed.

The cutting assembly is configured to cooperate with the balloon to cut the lesion site. In order to avoid damage to normal blood vessels of the cutting assembly in the process of pushing the cutting assembly along the guide wire and to improve the ability of passing the tortuous blood vessels, in this embodiment, the cutting assembly and the balloon 1 are assembled separately. When the balloon 1 is pushed to the target site, the cutting assembly moves close to the peripheral surface of balloon 1, and then the balloon 1 is expanded to apply a radial pressure to the cutting assembly, so that the cutting assembly performs the cutting on the diseased tissue under the action of the radial pressure.

Based on the above contemplation, the cutting assembly of the present embodiment includes a plurality of first support rings 30 arranged at intervals and blade groups 31 arranged on each of the first support rings 30. The first support rings 30 are sleeved on the outer tube g2 and arranged along an axial direction of the inner tube g1. Specifically, the number of first support rings 30 is determined according to the length of balloon 1, so that the total length of the first support rings 30 arranged from the first one to the last one can cover the entire balloon 1. The first support rings 30 are capable of generating radial elastic deformation and sliding freely so that the first support rings 30 can be pushed from the outer tube g2 to the balloon 1 (referring to FIG. 7), or from the balloon 1 to the outer tube g2. In addition, two adjacent blade groups 31 are connected with one another through a first flexible member 32, so that each blade group 31 is connected with the adjacent one as a whole, and may be freely bent based on the flexible characteristics of the first flexible members 32. Due to the flexible characteristics of the connection, different angles of the blade groups 31 may be adapted to follow the bending of the blood vessel, so as to easily pass through the tortuous blood vessel. The material of the first flexible member 32 in this embodiment is preferably one of silicone, TPU, Pebax, nylon, and the length of each first flexible member 32 is 1-10 mm.

The push-pull tube 5 is sleeved on the outer tube g2, and is slidable along the outer tube g2. The distal end of the push-pull tube 5 is connected with the blade group 31 through a second flexible member 6, so that the push-pull tube 5 can push each blade group 31 together with the first support ring 30 to the peripheral surface of the balloon 1, thereby the blade groups 31 may effectively cut the lesion site and then be pulled back from the balloon 1 together with the first support rings 30. In particular, the material of the push-pull tube 5 in the present embodiment may be any of nylon, Pebax, multilayer braided tube, or metal spiral cutting tube.

The tip 2 in the present embodiment has a hollow structure and is positioned at the distal end of the inner tube g1. The tip 2 has a taper structure to reduce the pushing resistance of the cutting balloon catheter in the blood vessel. A stopper 20 is provided at the proximal end of the tip 2 to prevent the cutting assembly from moving forward and disconnecting from the inner tube g1.

The proximal end of the protective bag 4 is connected with the push-pull tube 5, and the protective bag 4 is configured to encapsulate the balloon 1 and the cutting assembly, that is, the balloon 1 and the cutting assembly are wrapped by the protective bag 4, thus effectively reducing the risk of damage to normal blood vessels by the cutting assembly. When the cutting assembly is pushed to the balloon 1 by the push-pull tube 5, after the balloon is expanded, the blade groups 31 cut a section of the protective bag 4 opposite to the balloon 1 (i.e. the front section of the protective bag 4) so as to expose the blade groups 31 (referring to FIG. 8).

Figure 5:
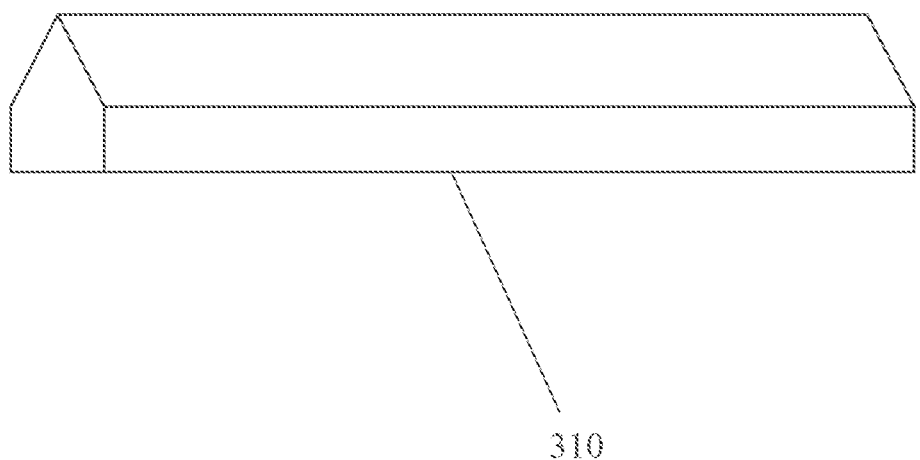
FIG. 5 is a perspective view of a blade according to the embodiment of the invention.

Optionally, as shown in FIGS. 2 and 5, the blade group 31 includes a plurality of blades 310 arranged at intervals along the peripheral surface of the first support ring 30. In this embodiment, each blade group 31 is configured with four blades 310, which are evenly distributed on the peripheral surface of the first supporting ring 30, so as to cut the pathological tissue in all directions around the periphery of the balloon 1. Specifically, the height of the blade 310 is 0.5 to 5 mm, and the length of the blade 310 is 1 to 50 mm.

It is understood that, each blade group 31 in the present embodiment may be configured with blade 310s with other amounts. For example, the amount of blade 310s may be 2, 3, 5, 6, 7, 8, 9, or 10, which is not limited here.

In a preferred embodiment, the amount of the blades 310 in the present embodiment is determined according to the length of the balloon 1.

The material of the blades 310 in the present embodiment is alloy, optionally may be pure metal, plastic, ceramic and other materials with higher hardness in other embodiments.

Figure 6:
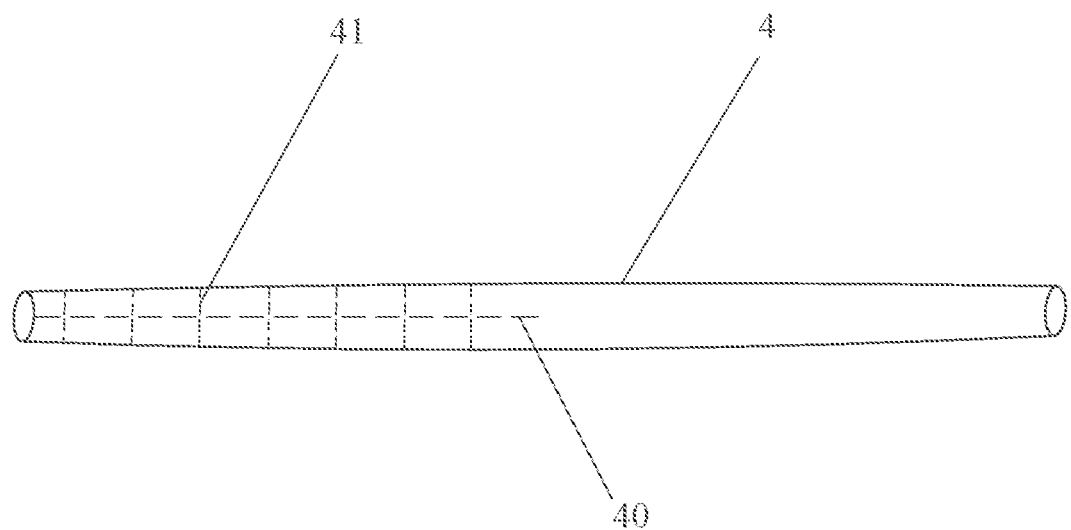
FIG. 6 is a structural diagram of a protective bag according to the embodiment of the invention.

Optionally, as shown in FIG. 6, the protective bag 4 is provided with a first cutting line 40 extended transversely, and the length of the first cutting line 40 is equivalent to that of the balloon 1. Such a configuration is beneficial to effectively cut the front section of the protective bag 4 when the cutting assembly is pushed to the peripheral surface of the balloon 1. Furthermore, the protective bag 4 is further provided with a plurality of second cutting lines 41 extended longitudinally and intersected with the first cutting line 40, each of the second cutting lines 41 is opposite to one of the blade groups 31 when the cutting assembly is pushed to the balloon 1. In the present embodiment, the first cutting line 40 and the second cutting lines 41 are formed by alternately dotting on the protective bag 4 (such as by laser dotting) along a preset trajectory. In such a way, the protective bag 4 can be easily broken when the blade groups 31 pass the intersection of the first cutting line 40 and the second cutting lines 41, so as to expose the blades in the blade groups 31.

Figure 4:
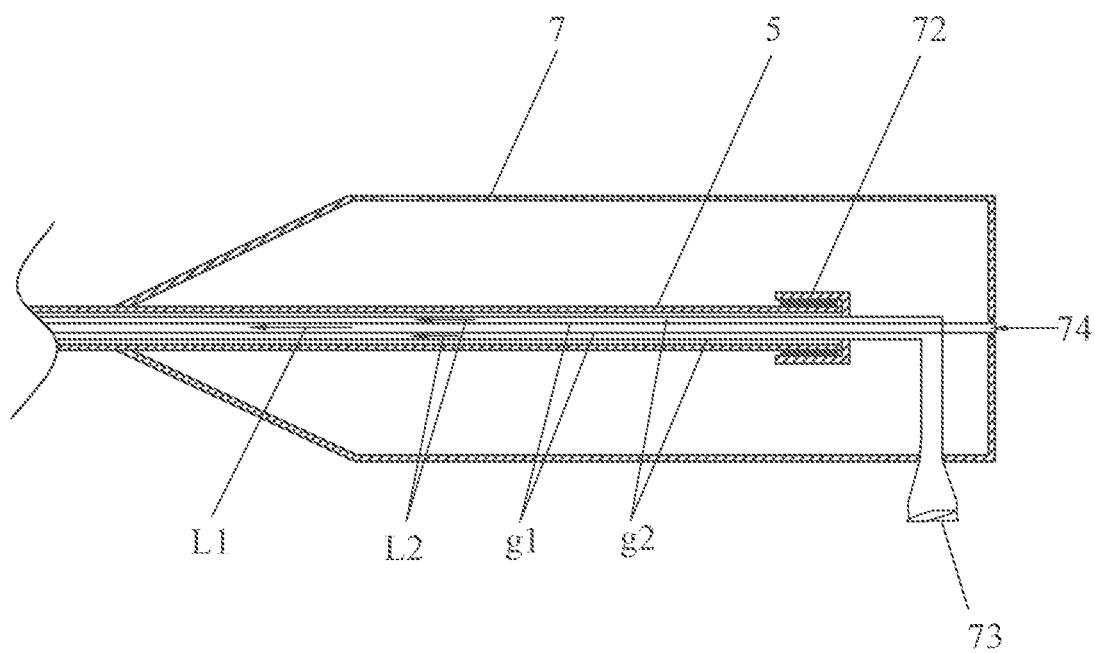
FIG. 4 is a cross section view of an operation end according to the embodiment of the invention.

As shown in FIG. 1 and FIG. 4, for facilitating the operation, the cutting balloon catheter in the present embodiment further includes an operating end 7 arranged on the proximal ends of the inner tube g1, the outer tube g2 and the push-pull tube 5. Specifically, the operating end 7 is provided with a control structure connected with the push-pull tube 5, the control structure is configured to drive the push-pull tube 5 to slide forward and backward along the outer tube g2, and the operating end 7 is further provided with a Luer taper 73 communicated with the pressure channel, that is, the outer tube g2 passes through the operating end 7 and is connected with the Luer taper 73. In the present embodiment, the outer tube g2 is manipulated by the control structure on the operating end 7 to slide forward and backward, thereby driving the cutting assembly to move forward and backward. The proximal end of the operating end 7 is further provided with a lumen (namely the port 74 receiving the wire guide channel L1) communicated with the inner tube g, to facilitate the passage of the guide wire.

Specifically, as shown in FIGS. 1 and 4, the control structure includes a slot 70, an operating handle 71 and a connecting member 72. The slot 70 is arranged on an outer wall of the operating end 7 and is communicated with a cavity of the operating end 7, and the slot 70 is extended laterally along the front and rear sliding direction of the outer tube g2. The operating handle 71 is arranged in the slot 70 and slidable along the slot 70, and the connecting member 72 is respectively connected with the push-pull tube 5 and the operating handle 72. When it's necessary to push or retract the cutting assembly, it's only required to push the operating handle 71 and slide it along the slot 70.

As shown in FIG. 1, the distal end of the push-pull tube 5 and the inner tube g1 of the balloon 1 are respectively provided with a positioning member. In the present embodiment, the distal end of the push-pull tube 5 is provided with a developer X1 as the positioning member, the proximal end and the distal end of the inner tube g1 in the balloon 1 are respectively provided with a developer X2/X3 as the positioning member. By the developer X1, the specific position of the moving end of the push-pull tube 5 can be effectively confirmed, so as to push the cutting assembly to the target position. By the developers X2 and X3, the position of the balloon 1 can be accurately positioned.

Referring to FIG. 3 again, the cutting assembly further includes a second support ring 33 located at the distal end of the first support rings 30, which is rigid and slidable. The second support ring 33 is connected with the blade group 31 adjacent to the second support ring 33 through the first flexible member 32, and the inner diameter of the second support ring 33 is greater than the inner diameter of the proximal end of the tip 2 and less than the outer diameter of the proximal end of the tip 2, so that the end wall at the proximal end of the tip 2 may be functioned as the stopper 20, which has simple structure and reliable effect. In the present embodiment, the second support ring 33 is a rigid structure, whose diameter will not change according to external conditions. As a result, the second support ring 33 may be always pressed against the end wall at the proximal end of the tip 2 when the blade groups 31 are subjected to radial pressure to perform a cutting action, so as to prevent blade groups 31 from moving beyond the tip 2.

Optionally, the proximal end of the tip 2 is further provided with a step 21, and the distal end of the protective bag 4 is attached to the step 21. With such a step 21, the protective bag 4 can be prevented from being damaged by impact when the cutting balloon catheter is pushed along the guide wire.

Furthermore, the surfaces of tip 2 and the outer tube g2 are respectively provided with a hydrophilic coating (not shown), which effectively reduces the friction resistance of tip 2 and the outer tube g2.

The procedure for interventional therapy using the cutting balloon catheter provided in the above embodiment follows.

First, the guide wire is sent to the target site along the blood vessel; then, the wire guide channel L1 of the balloon cutting catheter is sleeved on the guide wire and pushed along the guide wire until the balloon 1 is pushed to the target site. During the pushing process, the balloon 1 is in a collapsed state, as shown in FIG. 1. The cutting assembly is located on the outer tube g2 at the proximal end of the balloon 1, and both of the balloon 1 and the cutting assembly are wrapped in protective bag 4.

Then, when the balloon 1 is confirmed by the developers X2 and X3 to reach the target site, the operating handle 71 on the operating end 7 is pushed to move toward the distal end, to drive the push-pull tube 5 to guide to the distal end, so that the blade groups 31 are pushed to slide toward the balloon 1 along the outer tube g2.

Figure 7:
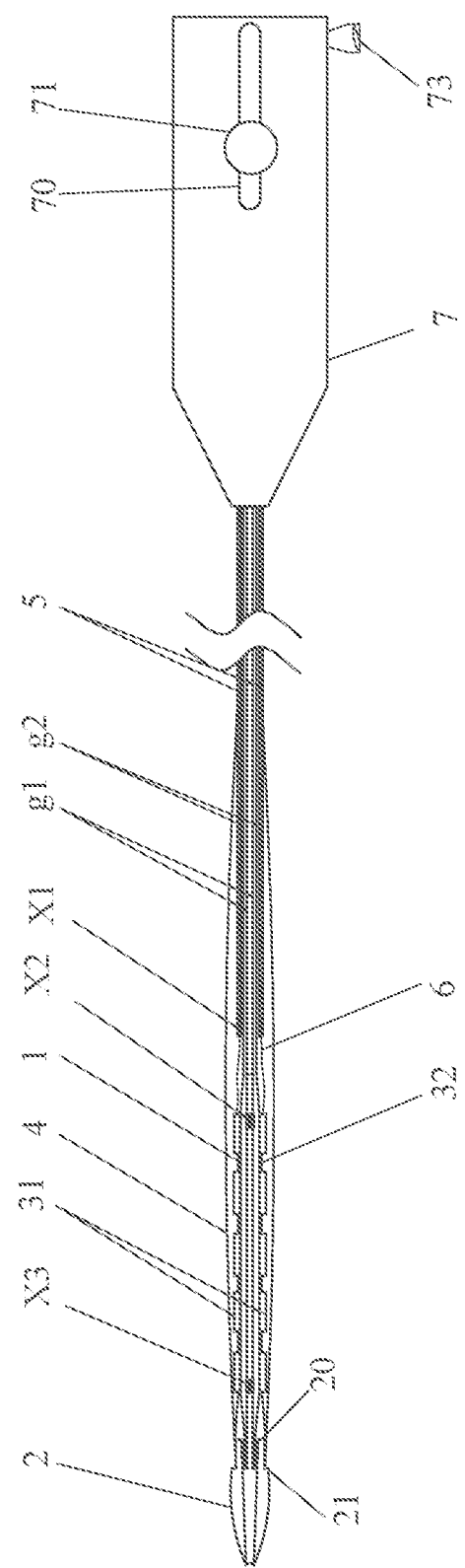
FIG. 7 is a plane view of the cutting balloon catheter according to the embodiment of the invention, wherein the cutting assembly is pushed to the outer position of the balloon.

When the movement is confirmed to move in place by the developer X1 at the distal end of the push-pull tube 5, the operation handle 71 is stopped. At this time, each blade group 31 is pushed to the position of the balloon 1, as shown in FIG. 7, and the second support ring 33 at the most front is blocked by the stopper 20 of the tip 2.

Figure 8:
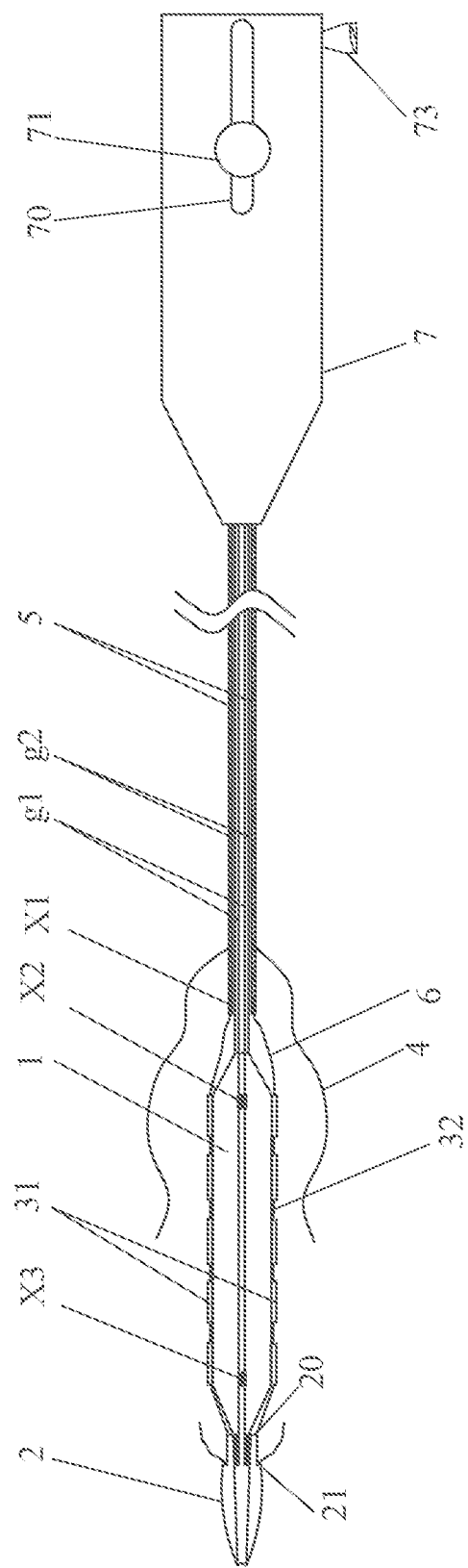
FIG. 8 is a schematic diagram of the cutting balloon catheter in working state according to the embodiment of the invention.

Then, inflating medium is filled into the pressure channel L2 through the Luer taper 73 on the operating end 7 to expand the balloon 1, as shown in FIG. 8. In the case of the expansion, the first support rings 30 generate an elastic deformation and the diameter thereof is increased, thereby applying a radial pressure on the blade groups 31 on the first support rings 30, causing the blade groups 31 to cut the protective bag 4 along the first cutting line 40 and the second cutting lines 41 to expose blade groups 31. Under the radial pressure, each blade 310 performs a cutting action on the diseased tissue. Then, the medium in the pressure channel L2 is extracted and then re-filled, so repeated for several times to complete the cutting treatment.

Finally, the balloon 1 is confirmed to be in the collapsed state, and the operating handle 71 is pushed in the reverse direction to drive the push-pull tube 5 to move toward the proximal end direction, so that the cutting assembly is driven by the second flexible member 6 to move along a direction from the balloon 1 to the outer tube g2, and finally moves to the space where the latter section of the protective bag 4 is located. Then, the entire cutting balloon catheter is drawn from the blood vessel along the guide wire.

Figure 9:
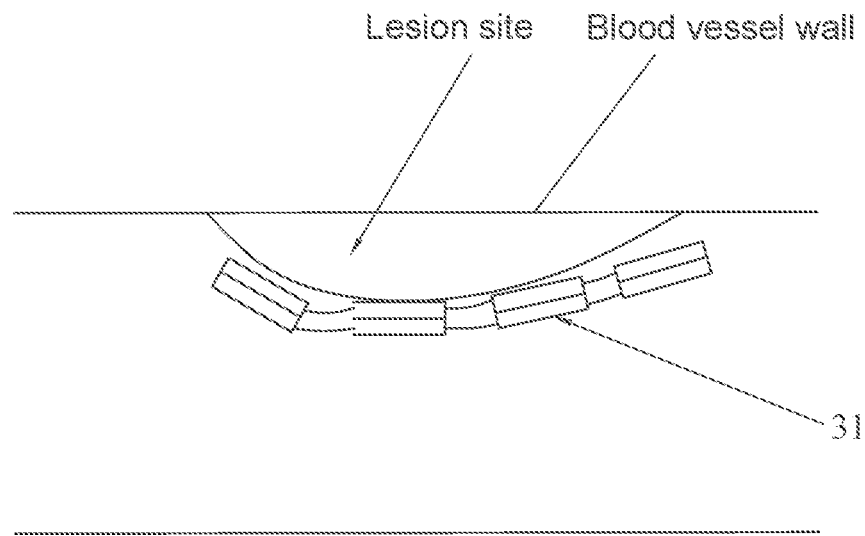
FIG. 9 is a schematic diagram of the working state showing the blade group cuts the vascular lesions according to the embodiment of the invention.
Figure 10:
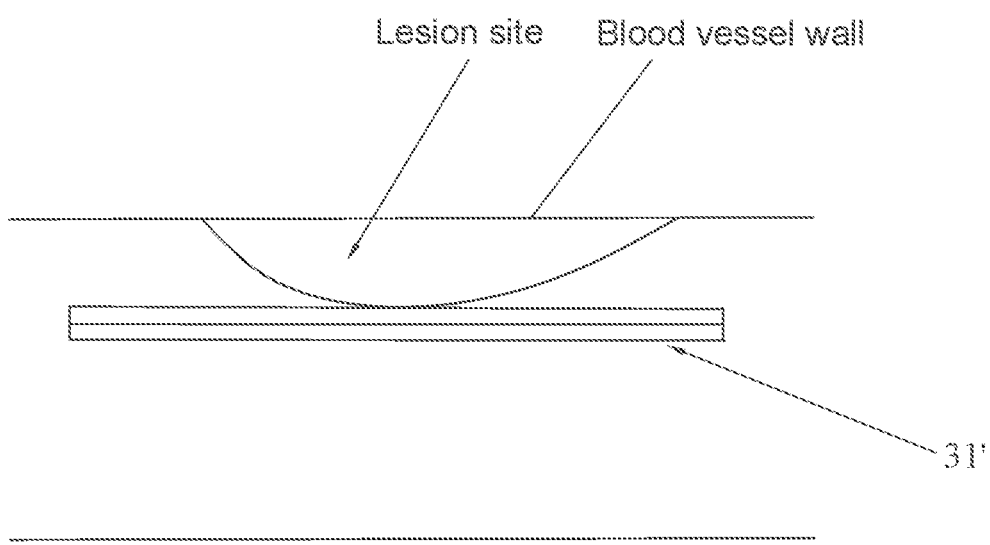
FIG. 10 is a schematic diagram of the working state showing a traditional blade group cuts the vascular lesions in the prior art.

By this token, in the cutting balloon catheter of the present invention, first, the cutting assembly is configured at the proximal end of the balloon 1 and arranged separately from the balloon 1, and the cutting assembly and the balloon 1 are packaged by the protective bag 4, further, the blade groups 31 are wrapped by the latter section of the protective bag 4 during the withdrawal process of the catheter after treatment, therefore, the cutting assembly is concealed in the protective bag 4 during the process of pushing the cutting assembly by the push-pull tube 5, which greatly reduces the risk of damage to normal blood vessels by the cutting assembly during the process of pushing. Second, for the cutting assembly, multiple blade groups 31 are connected together by flexible members and supported by a carrier that can generate radial elastic deformation, thus the cutting assembly has good overall bending performance, thereby improving the ability of cutting assembly to pass through tortuous blood vessels. In addition, as shown in FIG. 10, the traditional blade group 31 is not adaptive for a lesion site that is curved, as it cannot bend by following the curved surface of the lesion site. That's to say, the traditional blade group 31 may only cut a part of the lesion site, and the results may be unsatisfactory even after multiple cuts. Instead, as shown in FIG. 9, the cutting balloon catheter provided by the above embodiments of the invention is adaptive to follow the curved shape of the lesion site, since the angles between two adjacent blade groups 31 may be adjustable to follow the shape of the lesion site. Therefore, each blade group 31 may be attached to each curved position of the lesion site, so as to accurately cut the lesion site, and achieve good therapeutic effect. Further, excessive cutting on the lesion site is effectively avoided, complications such as perforation and restenosis are avoided, and it's applicable to the lesion site with a wider angle.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention.

What is claimed is:

1. A cutting balloon catheter with concealed blades, comprising:

an inner tube and an outer tube sleeved on the inner tube, and the inner tube having a distal end penetrating out of the outer tube;

a collapsible balloon, having a proximal end connected with the distal end of the outer tube and a distal end connected with the inner tube, and a pressure channel communicated with the balloon being formed by a gap between the outer tube and the inner tube;

a cutting assembly, comprising a plurality of first support rings sleeved on the outer tube and a blade group arranged on each of the first support rings, wherein the plurality of the first support rings are arranged along an axial direction of the inner tube and capable of generating radial elastic deformation and sliding freely, and two adjacent blade groups are connected with one another through a first flexible member;

a push-pull tube, sleeved on the outer tube and having a distal end connecting with the blade group close to the push-pull tube through a second flexible member;

a tip, being a hollow structure and arranged on the distal end of the inner tube, wherein the tip has a taper structure and a proximal end provided with a stopper for preventing a forward movement of the cutting assembly; and a protective bag, having a distal end connected with the proximal end of the tip and a proximal end connected with the push-pull tube, and configured to encapsulate the balloon and the cutting assembly; wherein when the cutting assembly is pushed to the balloon by the push-pull tube, after the balloon is expanded, the blade group cuts a section of the protective bag opposite to the balloon so as to expose the blade group.

2. The cutting balloon catheter with concealed blades according to claim 1, wherein the blade group comprises a plurality of blades arranged at intervals along an outer peripheral surface of each of first support rings.

3. The cutting balloon catheter with concealed blades according to claim 2, wherein each blade has a height of 0.5 mm to 5 mm and a length of 1 mm to 50 mm.

4. The cutting balloon catheter with concealed blades according to claim 1, further comprising an operating end arranged on the proximal ends of the inner tube, the outer tube and the push-pull tube, wherein the operating end is provided with a control structure connected with the push-pull tube, the control structure is configured to drive the push-pull tube to slide forward and backward along the outer tube, and the operating end is further provided with a Luer taper communicated with the pressure channel and a port communicated with a lumen of the inner tube.

5. The cutting balloon catheter with concealed blades according to claim 4, wherein the control structure comprises a slot, an operating handle and a connecting member, the slot is arranged on an outer wall of the operating end and communicated with a cavity of the operating end, the operating handle is arranged in the slot and slidable along the slot, and the connecting member is respectively connected with the push-pull tube and the operating handle.

6. The cutting balloon catheter with concealed blades according to claim 1, wherein the cutting assembly further comprises a second support ring located at the distal ends of all the first support rings and connected with the blade group through the first flexible member, the second support ring is rigid and capable of sliding freely, and an inner diameter of the second support ring is greater than an inner diameter of the proximal end of the tip and less than an outer diameter of the proximal end of the tip, so that a wall of the tip is served as the stopper.

7. The cutting balloon catheter with concealed blades according to claim 1, wherein the protective bag is provided with a first cutting line extended transversely and having a length equivalent to a length of the balloon.

8. The cutting balloon catheter with concealed blades according to claim 7, wherein the protective bag is further provided with a plurality of second cutting lines extended longitudinally and intersected with the first cutting line, each of the second cutting lines is opposite to one of the blade groups when the cutting assembly is pushed to the balloon.

9. The cutting balloon catheter with concealed blades according to claim 1, wherein the distal end of the push-pull tube and the inner tube of the balloon are respectively provided with a positioning member.

* * * * *